(12) United States Patent
Chang et al.

(10) Patent No.: US 7,691,624 B2
(45) Date of Patent: Apr. 6, 2010

(54) CANCER CELL DETECTING DEVICES

(75) Inventors: Ta-Chau Chang, Taipei (TW);
Cheng-Chung Chang, Danshuei Township, Taipei County (TW);
Chi-Chih Kang, Yongkang (TW);
Ji-Yen Cheng, Taipei (TW)

(73) Assignee: Academia Sinica (TW)

( * ) Notice: Subject to any disclaimer, the term of this patent is extended or adjusted under 35 U.S.C. 154(b) by 0 days.

(21) Appl. No.: 11/582,867

(22) Filed: Oct. 18, 2006

(65) Prior Publication Data

US 2007/0098233 A1 May 3, 2007

Related U.S. Application Data

(63) Continuation-in-part of application No. 11/131,905, filed on May 17, 2005, which is a continuation-in-part of application No. 10/690,984, filed on Oct. 22, 2003, now Pat. No. 6,979,738.

(60) Provisional application No. 60/788,903, filed on Apr. 4, 2006.

(51) Int. Cl.
*C12M 1/34* (2006.01)
*C12M 3/00* (2006.01)

(52) U.S. Cl. ............... 435/288.7; 435/4; 435/287.1; 435/287.2

(58) Field of Classification Search ............ 435/287.1, 435/287.2, 288.7, 4–6; 382/120
See application file for complete search history.

(56) References Cited

U.S. PATENT DOCUMENTS

| | | | |
|---|---|---|---|
| 6,121,008 A * | 9/2000 | Fitzpatrick et al. | 435/7.9 |
| 6,156,763 A | 12/2000 | Kerwin et al. | 514/279 |
| 6,325,623 B1 * | 12/2001 | Melnyk et al. | 433/29 |
| 7,160,896 B2 | 1/2007 | Neidle et al. | 514/297 |
| 2002/0182715 A1 * | 12/2002 | Chang et al. | 435/287.2 |
| 2003/0142302 A1 * | 7/2003 | Jiang | 356/301 |
| 2003/0235924 A1 * | 12/2003 | Adams et al. | 436/172 |

FOREIGN PATENT DOCUMENTS

JP  2002-172864  6/2002

OTHER PUBLICATIONS

Arthanari et al., "Fluorescent Dyes Specific for Quadruplex DNA", Nucleic Acids Research 26:3724-3728, 1998.
Chang et al., "A Carbazole Derivative Synthesis for Stabilizing the Quadruplex Structure", Journal of the Chinese Chemical Society 50:185-188, 2003.

(Continued)

*Primary Examiner*—Walter D Griffin
*Assistant Examiner*—Shanta G Doe
(74) *Attorney, Agent, or Firm*—Fish & Richardson P.C.

(57) ABSTRACT

This invention relates to a device for detecting cancer cells. The device includes a light source for generating light (e.g., a light emitting diode), a first optical filter selected from the group consisting of a band pass filter and a long pass filter, a second optical filter (i.e., a band pass filter) disposed between the light source and the first optical filter, and a sample receiver for receiving a sample. The sample receiver is disposed between the first and second optical filters. The first optical filter, the sample receiver, and the second optical filter are aligned so that light emitted from the light source passes sequentially through the second optical filter, the sample receiver, and the first optical filter.

28 Claims, 1 Drawing Sheet

OTHER PUBLICATIONS

Chang et al., "A Fluorescent Carbazole Derivative: High Sensitivity for Quadruplex DNA", Anal. Chem. 75:6177-6183, 2003.

Chang et al., "A Novel Carbazole Derivative, BMVC: a Potential Antitumor Agent and Fluorescence Marker of Cancer Cells", Chemistry & Biodiversity 1:1377-1384, 2004.

Chang et al., "Detection of Quadruplex DNA Structures in Human Telomeres by a Fluorescent Carbazole Derivative", American Chemical Society, EST:4.5 Analytical Chemistry A thru E, 2004.

Duan et al., Chemical Abstracts, 134:107619, 2000.

Duan et al., "Linear and Nonlinear Optical Properties of Novel Ionic Chromophores", Mat. Res. Soc. Symp. Proc. 598:BB3.31.1-BB3.31.6, 2000.

Krieg et al., Chemical Abstracts, 134:159223, 2000.

Kang et al., "Simple Method in Diagnosing Cancer Cells by a Novel Fluorescence Probe BMVC", Journal of the Chinese Chemical Society, 52:1069-1072, 2005.

Chang et al., "Verification of Antiparallel G-Quadruplex Structure in Human Telomeres by Using Two-Photon Excitation Fluorescence Lifetime Imaging Microscopy of the 3,6-Bis(1-methyl-4-vinylpyridinium)carbazole Diiodide Molecule", Analytical Chemistry, 78:2810-2815, 2006.

Chang et al., "A Fluorescent Carbazole Derivative: High Sensitivity for Quadruplex DNA", Analytical Chemistry, 75(22), 6177-6183, web release date Oct. 4, 2003.

Kelland, L., "Telomerase: Biology and Phase I Trials", Lancet Oncology, 2(2), 95-102, 2001.

Gowan, et al., "A G-Quadruplex-Interactive Potent Small-Molecule Inhibitor of Telomerase Exhibiting in Vitro and in Vivo Antitumor Activity", Molecular Pharmacology, 61(5), 1154-1162, 2002.

Li-Jen Liao, Chi-Chih Kang, I-Shiow Jan, Huei-Chin Chen, Chiung-Lin Wang, Pei-Jen Lou and Ta-Chau Chang; Improved diagnostic accuracy of malignant neck lumps by a simple BMVC staining assay; The Analyst, 2009. DOI:10.1039-b814417F.

Li-Jen Liao, Chi-Chih Kang, I-Shiow Jan, Huei-Chin Chen, Chiung-Lin Wang, Pei-Jen Lou and Ta-Chau Chang "Improved diagnostic accuracy of malignant neck lumps by a simple BMVC staining assay" *Analyst*, 2009, 134, pp. 708-711.

Nam W. Kim et al., Specific Association of Human Telomerase Activity with Immortal Cells and Cancer, Dec. 1994, *Science*, vol. 266, pp. 2011-2015.

* cited by examiner

SEQUENCE LISTING

```
<160> NUMBER OF SEQ ID NOS: 13

<210> SEQ ID NO 1
<211> LENGTH: 12
<212> TYPE: DNA
<213> ORGANISM: Artificial Sequence
<220> FEATURE:
<223> OTHER INFORMATION: Synthetically generated  oligonucleotide

<400> SEQUENCE: 1
atatatatat at                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetically generated  oligonucleotide

<400> SEQUENCE: 2
gcgcaattgc gc                                                          12

<210> SEQ ID NO 3
<211> LENGTH: 12
<212> TYPE: DNA
<213> ORGANISM: Artificial Sequence
<220> FEATURE:
<223> OTHER INFORMATION: Synthetically generated  oligonucleotide

<400> SEQUENCE: 3
gcgcgcgcgc gc                                                          12

<210> SEQ ID NO 4
<211> LENGTH: 10
<212> TYPE: DNA
<213> ORGANISM: Artificial Sequence
<220> FEATURE:
<223> OTHER INFORMATION: Synthetically generated  oligonucleotide

<400> SEQUENCE: 4
```

```
gggggggggg                                                              10

<210> SEQ ID NO 5
<211> LENGTH: 6
<212> TYPE: DNA
<213> ORGANISM: Artificial Sequence
<220> FEATURE:
<223> OTHER INFORMATION: Synthetically generated  oligonucleotide

<400> SEQUENCE: 5 tggggt                                                                   6

<210> SEQ ID NO 6
<211> LENGTH: 8
<212> TYPE: DNA
<213> ORGANISM: Artificial Sequence
<220> FEATURE:
<223> OTHER INFORMATION: Synthetically generated oligonucleotide

<400> SEQUENCE: 6 ttggggtt                                                                 8

<210> SEQ ID NO 7
<211> LENGTH: 8
<212> TYPE: DNA
<213> ORGANISM: Artificial Sequence
<220> FEATURE:
<223> OTHER INFORMATION: Synthetically generated oligonucleotide

<400> SEQUENCE: 7 ttttgggg                                                                 8

<210> SEQ ID NO 8
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 8
ttggggttgg gg                                                           12

<210> SEQ ID NO 9
<211> LENGTH: 15
<212> TYPE: DNA
<213> ORGANISM: Artificial Sequence
<220> FEATURE:
<223> OTHER INFORMATION: Synthetically generated oligonucleotide

<400> SEQUENCE: 9
ggttggtgtg gttgg                                                        15

<210> SEQ ID NO 10
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 10
ggggttttgg gg                                                           12

<210> SEQ ID NO 11
<211> LENGTH: 28
<212> TYPE: DNA
<213> ORGANISM: Artificial Sequence
```

```
                        -continued

<220> FEATURE:
<223> OTHER INFORMATION: Synthetically generated oligonucleotide

<400> SEQUENCE: 11
ggggttttgg ggttttgggg ttttgggg                                    28

<210> SEQ ID NO 12
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 12
ttagggttag gg                                                     12

<210> SEQ ID NO 13
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 13
ttagggttag ggttagggtt aggg                                        24
```

CANCER CELL DETECTING DEVICES

CROSS REFERENCE TO RELATED APPLICATIONS

Under 35 U.S.C. § 120, this application is a continuation-in-part of and claims priority to U.S. Utility Application Ser. No. 11/131,905, filed May 17, 2005, which in turn is a continuation-in-part of and claims priority to U.S. Utility Application Ser. No. 10/690,984, filed Oct. 22, 2003 now U.S. Pat. No. 6,979,738. Under 35 U.S.C. § 119, this application claims priority to U.S. Provisional Application Ser. No. 60/788,903, filed Apr. 4, 2006. The contents of all of the prior applications are incorporated herein by reference.

BACKGROUND

Telomeres, the ends of chromosomes, are essential for the stability and replication of eukaryotic chromosomes. See, e.g., Williamson J. R., *Annu. Rev. Biophys. Biomol. Struct.*, 1994, 23:703. Telomeric sequences are shortened during cell division since DNA synthesis cannot fully replicate the extreme ends of chromosomes. A reduction in the telomere length to a critical level can lead to genomic instability, aberrant chromosome fusion, and cellular senescence. See, e.g., Harley et al., *Curr. Opin. Genet. Dev.*, 1995, 5:249. In contrast, telomeres of tumor cells do not shorten during cell replication due to the presence of a telomerase, which allows adding nucleotides to telomeric DNA at the ends of chromosomes. See, e.g., Feng et al., *Science*, 1995, 269:1236. Telomerase is expressed in more than 85% of tumor cells, but not in most somatic cells. See Harley et al., *Nature*, 1990, 345:458. Thus, telomerase is becoming a promising target for cancer diagnosis and chemotherapy. See Blackburn E. H., *Nature*, 1991, 350:569.

Telomeres generally consist of many tandem repeats of guanine-rich (G-rich) motifs, such as $T_2AG_3$ in human telomeres. See Morin GB., Cell, 1989, 59:521. It is shown in in vitro assays that the 3'-overhang G-rich single strand adopts an intramolecular G-quadruplex structure. The quadruplex structure is stabilized by $\pi$-$\pi$ interaction of a cyclic G-quartet, formed through Hoogsteen hydrogen bonding. See Gellert et al., *Proc. Natl. Acad. Sci. USA*, 1962, 48:2013. Since folding telomeric DNA into G-quadruplexes has been shown to inhibit telomerase activities in vitro, G-quadruplexes have also been considered as potential targets for antitumor agents. See Zahler et al., *Nature*, 1991, 350:718.

SUMMARY

This invention is based on the unexpected discovery that certain carbazole compounds can thermally stabilize G-quadruplexes of human telomeres. Further, when bound with cancer cells, the carbazole compounds can emit fluorescence upon excitation and is the basis for a simple, rapid, robust, non-invasive, and low cost device for detecting cancer cells.

In one aspect, this invention features a device for detecting cancer cells. The device includes a light source for generating light (e.g., a light emitting diode), a first optical filter selected from the group consisting of a band pass filter and a long pass filter, a second optical filter (i.e., a band pass filter) disposed between the light source and the first optical filter, and a sample receiver for receiving a sample. The sample receiver is disposed between the first and second optical filters. The first optical filter, the sample receiver, and the second optical filter are aligned so that light emitted from the light source passes sequentially through the second optical filter, the sample receiver, and the first optical filter.

In another aspect, this invention features carbazole compounds of formula (I):

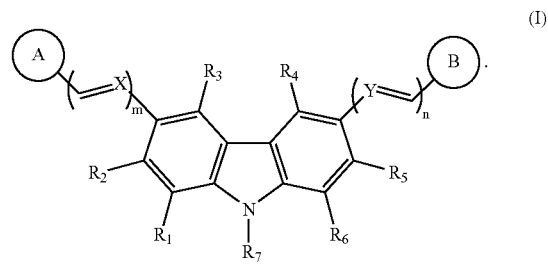

In formula (I), each of rings A and B, independently, is heteroaryl containing at least one nitrogen atom; each of X and Y, independently, is CH or N; each of $R_1$-$R_6$, independently, is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl, OH, $C_1$-$C_6$ alkoxy, aryloxy, heteroaryloxy, $NH_2$, $C_1$-$C_6$ alkylamino, $C_1$-$C_{12}$ dialkylamino, arylamino, diarylamino, or halogen; $R_7$ is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl; and each of m and n, independently, is 1, 2, or 3.

A subset of the above-described carbazole compounds features that each of rings A and B is heteroaryl containing one or two nitrogen atoms. In these compounds, each of m and n is 1; each of $R_1$-$R_7$ is H; and each of X and Y is CH or N.

The term "alkyl" refers to a saturated, linear or branched hydrocarbon moiety, such as $CH_3$, —$CH_2$—, or branched $C_3H_7$. The term "alkenyl" refers to a linear or branched, non-aromatic hydrocarbon moiety having at least one double bond, such as —CH=$CH_2$ or —CH=CH—. The term "alkynyl" refers to a linear or branched, non-aromatic hydrocarbon moiety having at least one triple bond, such as —C≡CH or —C≡C—. The term "cycloalkyl" refers to a saturated cyclic hydrocarbon moiety, such as cyclohexyl. The term "heterocycloalkyl" refers to a saturated cyclic moiety having at least one ring heteroatom, such as 4-tetrahydropyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "alkoxy" refers to a linear or branched, saturated or unsaturated, non-aromatic hydrocarbon moiety containing an oxygen radical, such as —$OCH_3$ or —OCH=$C_2H_5$. The term "aryloxy" refers to a moiety having at least one aromatic ring and an oxygen radical bonded to the aromatic ring, such as phenoxy. The term "heteroaryloxy" refers to a moiety having at least one aromatic ring that contains at least one ring heteroatom and an oxygen radical bonded to the aromatic ring, such as 4-pyrindinoxy.

Alkyl, alkenyl, alkynyl, cycloalkyl, heterocycloalkyl, aryl, heteroaryl, alkoxy, aryloxy, heteroaryloxy, alkylamino, dialkylamino, arylamino, and diarylamino mentioned herein include both substituted and unsubstituted moieties. Possible substituents on cycloalkyl, heterocycloalkyl, aryl, heteroaryl, aryloxy, heteroaryloxy, arylamino, and diarylamino include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, cyano, nitro, acyl, acyloxy, carboxyl, and carboxylic ester. On the other hand, possible substituents on alkyl, alkenyl, alkynyl, alkoxy, alkylamino, and dialkylamino include all of the above-recited substituents except $C_1$-$C_{10}$ alkyl, $C_2$-$C_{10}$ alkenyl, and $C_2$-$C_{10}$ alkynyl. Cycloalkyl and heterocycloalkyl can also be fused with aryl or heteroaryl.

The carbazole compounds described above include the compounds themselves, as well as their salts and their prodrugs, if applicable. A salt, for example, can be formed between an anion and a positively charged group (e.g., ammonium) on a carbazole compound. Suitable anions include chloride, bromide, iodide, sulfate, sulfite, perchlorate, hexafluorophosphate, nitrate, phosphate, citrate, methanesulfonate, trifluoroacetate, and acetate. Likewise, a salt can also be formed between a cation and a negatively charged group (e.g., carboxylate) on a carbazole compound. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active carbazole compounds.

In another aspect, this invention features a method for stabilizing a G-quadruplex of a human telomere or a telomere of other mammals. The method includes contacting a telomere with a carbazole compound of the same formula shown above. This method can be used to treat any telomerase-related diseases in which inhibiting telomerase activities is desired. In addition, this method can be used for in vitro assays (e.g., identifying a G-quadruplex of a telomere) or in vivo animal model testing or screening the efficacy of a carbazole compound mentioned above as a drug for treating telomerase-related diseases (e.g., cancer).

In another aspect, this invention features a method for detecting cancer cells in a subject (e.g., a mammal). The method includes (1) contacting a plurality of cells in a sample obtained from the subject with a compound of the formula shown above, and (2) calculating the percentage of the cells that emit florescence upon irradiation with an excitation light. If the percentage is above a pre-set value, the subject is determined to contain cancer cells.

In another aspect, this invention features a method for detecting cancer cells in a subject. The method includes (1) providing cells from a sample obtained from the subject; (2) contacting the cells with a dye (e.g., acridine orange, methylene blue, or 4',6-diamidino-2-phenylindole) to non-discriminatingly stain all cells and a compound of the formula (I) to discriminatingly stain cancer cells, if any; and (3) determining the ratio between the number of cells stained with the compound of formula (I) and the number of cells stained with the dye. If the ratio is above a pre-set value (e.g., 0.05 or 0.08), the subject is determined to have cancer cells.

In another aspect, this invention features a method for detecting cancer cells in a subject. The method includes (1) providing cells from a sample obtained from the subject; (2) contacting the cells with a compound of formula (I) to discriminatingly stain cancer cells, if any; (3) passing the cells in a channel; and (4) monitoring fluorescence emitted by the stained cells, if any. The subject is determined to contain cancer cells if fluorescence is detected. The passing step can be conducted in a flow cytometer.

In still another aspect, this invention features a method for treating cancer. The method includes administering to a subject in need thereof an effective amount of a compound of the formula shown above. "Treating" mentioned herein refers to administering one or more carbazole compounds in an effective amount to a subject, who has a telomerase-related disease (e.g., cancer), a symptom of such a disease, or a predisposition toward such a disease, with the purpose to confer a therapeutic effect, e.g., to cure, relieve, alter, affect, ameliorate, or prevent the telomerase-related disease, the symptom of it, or the predisposition toward it. "An effective amount" mentioned herein refers to the amount of one or more carbazole compounds described above that is required to confer a therapeutic effect on a treated subject.

In addition, this invention encompasses a pharmaceutical composition that contains an effective amount of at least one of the above-mentioned carbazole compounds and a pharmaceutically acceptable carrier.

Also within the scope of this invention is a composition containing one or more of the carbazole compounds described above for use in treating a telomerase-related disease, and the use of such a composition for the manufacture of a medicament for the just-mentioned treatment.

The details of one or more embodiments of the invention are set forth in the drawings and the description below. Other features, objects, and advantages of the invention will be apparent from the drawings, the description, and the claims.

DESCRIPTION OF DRAWINGS

Like reference symbols in the various drawings indicate like elements.

DETAILED DESCRIPTION

Figure 1:
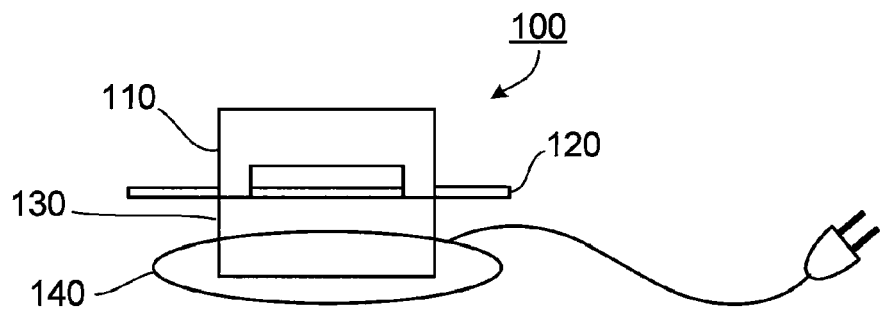
FIG. 1 is a side view of a device for detecting cancer cells.

An embodiment of a cancer cell-detecting device of this invention is illustrated in FIGS. 1, 2, 3, and 4. More specifically, FIG. 1 shows that device 100 includes first optical filter 110, sample receiver 120, second optical filter 130, and light source 140. During use, a sample containing cells obtained from a subject (e.g., by needle biopsy) can be first stained with a fluorescence dye (e.g., compound 2 described below). The sample can then be placed on sample receiver 120, which in turn can be inserted into device 100. After light source 140 is turned on, a portion of the light emitted from light source 140 transmits through second optical filter 130 and reaches the sample. Cells stained with the dye in the sample are excited by the transmitted light and emit fluorescence light, a portion of which transmits through first optical filter 110 and then is recorded by a detector or observed by eyes. Light emitted from light source 140 that transmits through the sample is blocked by first optical filter 111.

Figure 2:
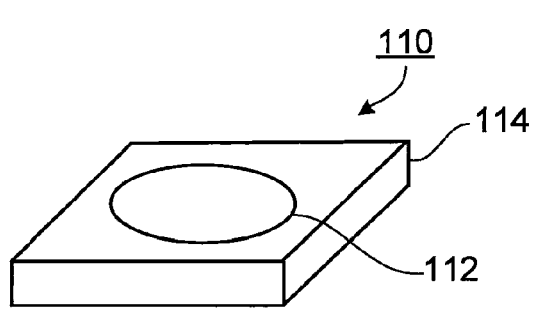
FIG. 2 is a perspective view of a first optical filter used in the device shown in FIG. 1.

As shown in FIG. 2, first optical filter 110 includes circular filter component 112 and filter component holder 114. First optical filter 110 can be a long pass filter (e.g., a 520 nm long pass filter) or a band pass filter (e.g., a 550 nm band pass filter). Long pass filters and band pass filters are well known in the art and are commercially available. First optical filter 110 blocks a portion of the fluorescence light emitted from the sample and the light emitted from light source 140 that transmits through the sample, thereby minimizing the background noise and improving signal to noise ratio of the fluorescence light. The type of first optical filter 110 can be selected based on various factors, such as the wavelength of the fluorescence light emitted from the sample, the wavelength of the light emitted from the light source, and the absorption characteristics of the fluorescence dye.

Sample receiver 120 can be planar (e.g., a glass slide) or tubular (e.g., a tube). When a sample contains a very small amount of cancer cells (e.g., a sample obtained from a subject having early stage cancer), tubular sample receiver 120 is preferred since it increases the chances of cancer cell aggregation. When stained with a fluorescence dye, aggregated cancer cells emit much stronger fluorescence upon excitation and are easier to be detected. Tubular sample receiver 120 can have a diameter from 200 µm to 400 µm. Sample receiver 120 can also include a holder (not shown in FIGS. 1-4) for holding the receiver.

Figure 3:
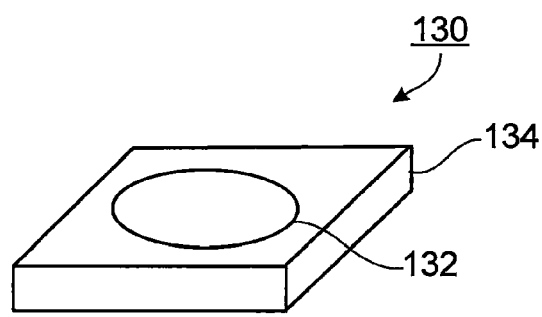
FIG. 3 is a perspective view of a second optical filter used in the device shown in FIG. 1.

As shown in FIG. 3, second optical filter 130 includes circular filter component 132 and filter component holder 134. Second optical filter 130 typically is a band pass filter (e.g., a 470 nm band pass filter). It selects the excitation wavelength by allowing only light of a certain wavelength or a certain range of wavelength to pass through. The type of second optical filter 130 can be selected based on various factors, such as the wavelength of the light emitted from the light source and the absorption characteristics of the fluorescence dye.

Figure 4:
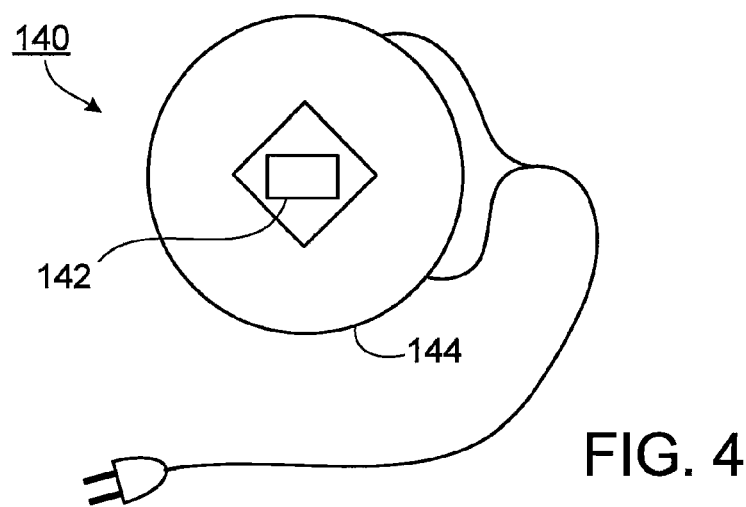
FIG. 4 is a top view of a light source used in the device shown in FIG. 1.

As shown in FIG. 4, light source 140 includes light emitting diode 142 and support 144. Light emitting diode 142 can emit lights having a wavelength of 460 nm to 475 nm. Light source 140 can also be a light bulb or a laser.

The fluorescence light emitted from a sample can be detected by eyes without using a detector. If desired, device 100 can further include a detector capable of detecting fluorescence light emitted from a sample. Examples of detectors include a camera and an ultrasonic detector (such as a device that converts light with an intensity above a certain level to ultrasonic signals). The results obtained by the detector can be saved as a record or for further analysis.

Preferably, device 100 is compact in size. For example, the distance between a point on light source 140 and a point on second optical filter 130 can be from 5 to 7 mm (e.g., from 5.5 to 6.5 mm), the distance between a point on second optical filter 130 and a point on sample receiver 120 is from 0.1 to 2 mm (e.g., 0.5 to 1 mm), and the distance 5 between a point on sample receiver 120 and a point on first optical filter 110 is from 6 to 8 mm(e.g., 6.5 to 7.5 mm).

Device 100 can be used by a health professional in a hospital or a patient at home.

It can be used to detect cells of many types of cancer as long as a sample containing a sufficient amount of cancer cells can be obtained. For example, a sample can be obtained from saliva, blood, cervical smear, or an internal organ (e.g., by needle biopsy) from a patient. The presence of cells in a sample can be confirmed by staining the sample with a non-discriminating dye (e.g., acridine orange) and observing fluorescence light, if any, using device 100 described above.

Device 100 does not involve sophisticated equipments and therefore can be manufactured inexpensively. Further, device 100 is compact in size and can be easily carried by a user (e.g., a health professional or a patient) for performing a test at a place convenient to the user. The test result is instantly available to the user after a test has been performed.

Shown below are exemplary carbazole compounds, compounds 1-8, of this invention that can be used as a discriminating dye in a device described above.

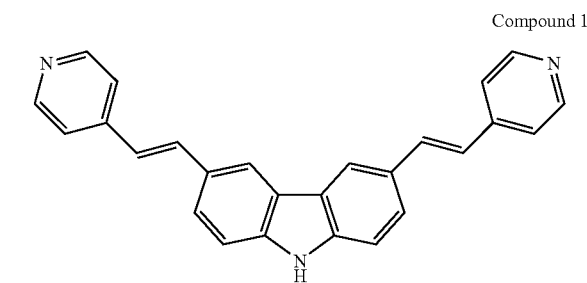

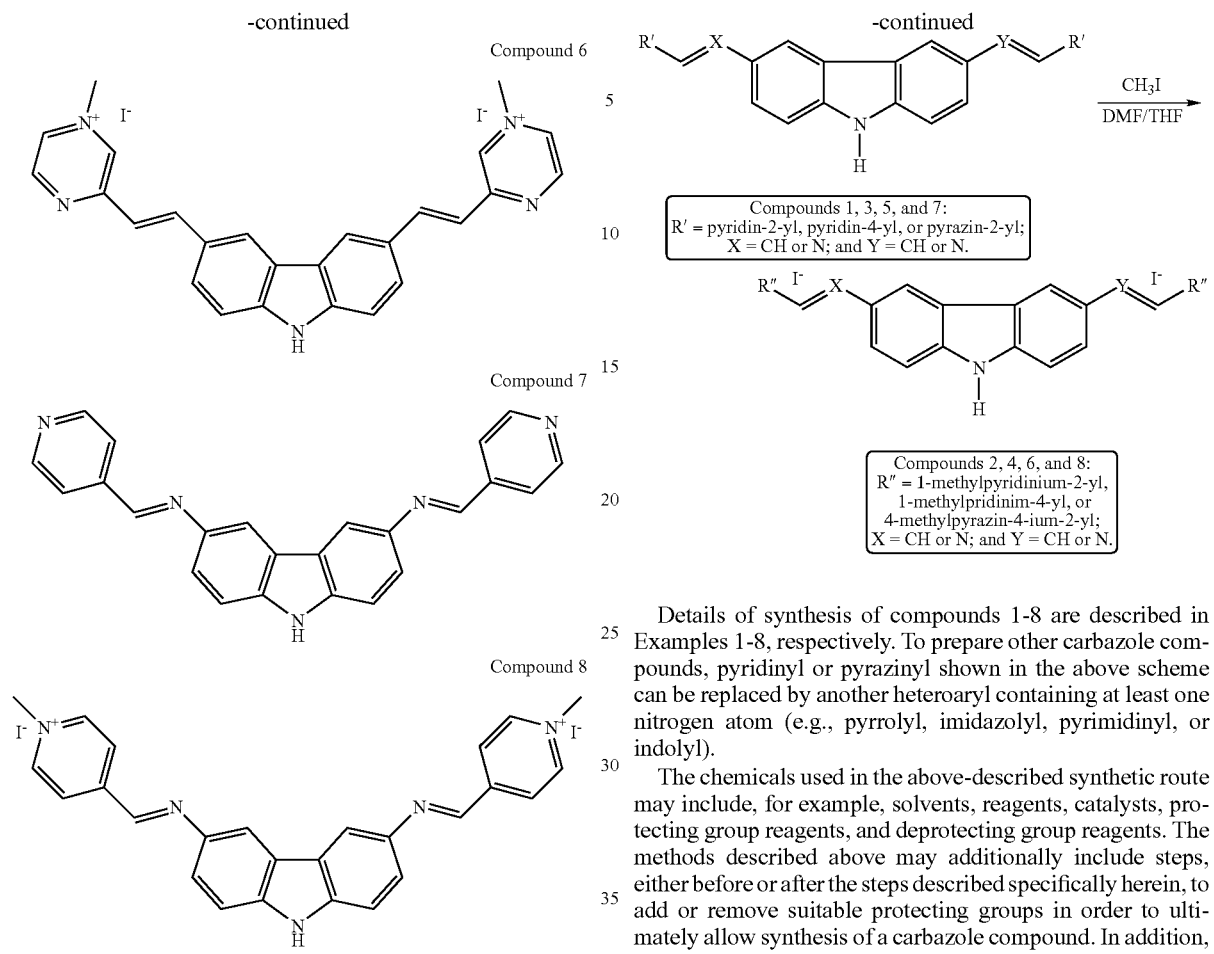

The carbazole compounds described above can be prepared by methods well known in the art, as well as by the synthetic routes disclosed herein. For example, one can react 3,6-dibromocarbazole with an olefin containing a heteroaryl group with at least one nitrogen atom in the presence of a palladium catalyst to produce an intermediate, 3,6-bis(heteroaryl-vinyl)-carbazole. The intermediate can then be treated with methyl iodide to produce a corresponding iodide salt. As another example, one can react 3,6-diaminocarbazole with a formaldehyde containing a heteroaryl group with at least one nitrogen atom to produce an intermediate, 3,6-bis(heteroaryl-methylidene-imino)-carbazole. Similarly, this intermediate can also be converted to a corresponding iodide salt upon treating with methyl iodide.

Shown below is a scheme that depicts the synthesis of compounds 1-8 mentioned above.

Details of synthesis of compounds 1-8 are described in Examples 1-8, respectively. To prepare other carbazole compounds, pyridinyl or pyrazinyl shown in the above scheme can be replaced by another heteroaryl containing at least one nitrogen atom (e.g., pyrrolyl, imidazolyl, pyrimidinyl, or indolyl).

The chemicals used in the above-described synthetic route may include, for example, solvents, reagents, catalysts, protecting group reagents, and deprotecting group reagents. The methods described above may additionally include steps, either before or after the steps described specifically herein, to add or remove suitable protecting groups in order to ultimately allow synthesis of a carbazole compound. In addition, various synthetic steps may be performed in an alternate sequence or order to give the desired carbazole compounds. Synthetic chemistry transformations and protecting group methodologies (protection and deprotection) useful in synthesizing applicable carbazole compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A carbazole compound thus synthesized can be further purified by a method such as column chromatography, high-pressure liquid chromatography, or recrystallization.

Note that the carbazole compounds contain at least two double bonds, and may further contain one or more asymmetric centers. Thus, they can occur as racemates and racemic mixtures, single enantiomers, individual diastereomers, diastereomeric mixtures, and cis- or trans- or E- or Z- double bond isomeric forms. All such isomeric forms are contemplated.

Also within the scope of this invention is a pharmaceutical composition contains an effective amount of at least one carbazole compound described above and a pharmaceutical acceptable carrier.

Further, this invention covers a method for stabilizing a G-quadruplex of a human telomere or a telomere of other mammals. This method can be used to treat a subject with telomerase-related diseases (e.g., cancer) by administering to it an effective amount of one or more of carbazole compounds. Such a subject can be identified by a health care professional based on results from any suitable diagnostic method.

This invention also covers a method for detecting cancer cells in a subject by contacting cells with a certain concentration of a carbazole compound described above and calculating the percentage of the cells that emit fluorescence upon irradiation with an excitation light. If the percentage is above a pre-set value (e.g., 30%), the subject is determined to contain cancer cells. The pre-set value can be determined empirically and varies depending upon the concentration and the type of the carbazole compound used and the type of the cells targeted. For example, the pre-set value can be determined by respectively contacting cancer cells and normal cells with one of the carbazole above-described compounds and subsequently calculating the percentages of the cancer cells and normal cells that emit fluorescence upon irradiation of an excitation light. The pre-set value can then be selected statistically such that it is greater than the percentage of the normal cells that emit fluorescence, but the same as or lower than the percentage of the cancer cells that emit fluorescence. This method can be done by passing the cells in a channel (e.g., in a flow cytometer), and monitoring fluorescence, if any, emitted by the stained cells.

This invention also covers a method for detecting cancer cells in a subject by contacting cells with a dye (e.g., acridine orange, methylene blue, or 4',6-diamidino-2-phenylindole) to non-discriminatingly stain all cells and a compound of the formula (I) to discriminatingly stain cancer cells, if any, and determining the ratio between the number of cells stained with the compound of formula (I) and the number of cells stained with the dye. If the ratio is above a pre-set value (e.g., 0.05 or 0.08), the subject is determined to have cancer cells. If the fluorescence light emitted from the cells stained with the non-discriminating dye and that emitted from the cells stained with the discriminating dye have substantially different wavelengths, a sample can be stained by both dyes and the fluorescence light can be detected at their corresponding wavelengths by a detector. On the other hand, if the fluorescence light emitted from the cells stained with the non-discriminating dye and that emitted from the cells stained with the discriminating dye have similar wavelengths, two identical samples can each be stained by the non-discriminating dye or the non-discriminating dye. Each sample can then be excited to determine the total number of cells in each sample and the number of cancer cell in each sample. The ratio between the number of cancer cells and the total number of cells can then be calculated.

When using the method of this invention to treat a subject with telomerase-related disease, one can determine effective doses by methods well known in the art. For example, the interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the carbazole compounds can range from about 0.1 mg/Kg to about 100 mg/Kg. Effective doses will vary, as recognized by those skilled in the art, depending on, e.g., the types of diseases treated, route of administration, excipient usage, and the possibility of co-usage with other therapeutic treatment.

To treat a telomerase-related disease, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, intraperitoneal, intratracheal or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow # 10.

The carbazole compounds of this invention can be preliminarily screened for their efficacy in stabilizing G-quadruplexes by in vitro assays (See Example 9 below). Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of compound 1:
3,6-Bis-(2-pyridin-4-yl-vinyl)-9H-carbazole

Compound 1 was prepared following the procedures described below:

3,6-Dibromocarbazole (1.63 g, 5 mmol, Aldrich) was added into a high pressure flask containing a mixture of palladium(II) acetate (15 mg, Strem) and tri-o-tolyl phosphine (150 mg, Aldrich). To this flask was added a mixed solvent (triethylamine 5 mL/acetonitrile 15 mL) and 4-vinylpyridine (2 g, 20 mmol, Merck). The flask was sealed after bubbling nitrogen for 10 minutes. After keeping the reaction at ~105° C. for three days, precipitate was collected and then washed with $H_2O/CH_2Cl_2$ twice. The resultant insoluble solid was filtered and dissolved in THF, then dried over anhydrous $MgSO_4$. Compound 1 was collected as a yellow powder by filtration after recrystallization from THF filtrate (Yield: 62%, mp>300° C.).

$^1$H NMR ($CD_3OD$): δ 8.42 (d, J=5.7 Hz, 4H), 8.25 (s, 2H), 7.65 (d, J=8.4 Hz, 2H), 7.56 (d, J=16.2 Hz, 2H), 7.45 (d, J=5.7 Hz, 4H), 7.42 (d, J=8.4 Hz, 2H), 7.70 (d, J=16.2 Hz, 2H). EA (373+1.5$H_2O$): calc (obs %) C: 83.64 (78.20), H: 5.09 (5.14), N: 11.26 (10.38).

EXAMPLE 2

Preparation of compound 2: 3,6-bis-(2-(1-methylpyridinium-4-yl)-vinyl)-9H-carbazole diiodide Compound 2 was prepared following the procedures described below:

After refluxing 3,6-di(4-vinylpyridine) carbazole obtained in Example 1 with excess $CH_3I$ in acetone, compound 2 was collected as an orange-red powder by filtration after recrystallization from methanol twice (Yield: 92%, mp>300° C.).

$^1$H NMR (DMSO-d6): δ 8.77 (d, J=6.9 Hz, 4H), 8.59 (s, 2H), 8.19 (d, J=6.9 Hz, 4H), 8.20 (d, J=15.9 Hz, 2H), 7.90 (d, J=8.7 Hz, 2H), 7.64 (d, J=8.7 Hz, 2H),7.53 (b, J=15.9 Hz, 2H). EA (657+1.0$H_2O$): calc (obs %) C: 51.14 (49.87), H: 3.81 (4.03), N: 6.39 (6.32).

EXAMPLE 3

Preparation of compound 3:
3,6-bis-(2-pyridin-2-yl-vinyl)-9H-carbazole

Compound 3 was prepared in a manner similar to that described in Example 1.

EXAMPLE 4

Preparation of compound 4: 3,6-bis-(2-(1-methylpyridinium-2-yl)-vinyl)-9H-carbazole diiodide Compound 4 was prepared in a manner similar to that described in Example 2.

EXAMPLE 5

Preparation of compound 5:
3,6-bis-(2-pyrazin-2-yl-vinyl)-9H-carbazole

Compound 5 was prepared in a manner similar to that described in Example 1.

EXAMPLE 6

Preparation of compound 6: 3,6-bis-(2-(4-methylpyrazin-4-ium-2-yl)-vinyl)-9H-carbazole diiodide Compound 6 was prepared in a manner similar to that described in Example 2.

EXAMPLE 7

Preparation of compound 7: N,N'-bis-(pyridin-4-ylmethylidene)-9H-carbazole-3,6-diamine Compound 7 was prepared in a manner similar to that described in Example 1.

EXAMPLE 8

Preparation of compound 8: N,N'-bis-((1-methylpyridinium-4-yl)methylidene)-9H-carbazole-3,6-diamine diiodide Compound 8 was prepared in a manner similar to that described in Example 2.

EXAMPLE 9

Binding between carbazole compounds and DNA duplexes and quadruplexes

Calf thymus (ct-DNA) and oligonucleotides AT, LD, GC, G10, LQ1, LQ2, LQ4, Tet12, Apt, Oxy12, Oxy28, Hum12, and Hum24 were purchased from Applied Biosystems. The sequences of these oligonucleotides are listed below:

| | | |
|---|---|---|
| AT: | 5'-(AT)$_6$-3' | (SEQ ID NO:1) |
| LD: | 5'-GCGCA2T2GCGC-3' | (SEQ ID NO:2) |
| GC: | 5'-(GC)$_6$-3' | (SEQ ID NO:3) |
| G10: | 5'-d(G)$_{10}$-3' | (SEQ ID NO:4) |
| LQ1: | 5'-TG$_4$T-3' | (SEQ ID NO:5) |
| LQ2: | 5'-T$_2$G$_4$T$_2$-3' | (SEQ ID NO:6) |
| LQ4: | 5'-T$_4$G$_4$-3' | (SEQ ID NO:7) |
| Tet12: | 5'-(T$_2$G$_4$)$_2$-3' | (SEQ ID NO:8) |
| Apt: | 5'-G$_2$T$_2$G$_2$TGTG$_2$T$_2$G$_2$-3' | (SEQ ID NO:9) |
| Oxy12: | 5'-G$_4$T$_4$G$_4$-3' | (SEQ ID NO:10) |
| Oxy28: | 5'-G$_4$(T$_4$G$_4$)$_3$-3' | (SEQ ID NO:11) |
| Hum12: | 5'-(T$_2$AG$_3$)$_2$-3' | (SEQ ID NO:12) |
| Hum24: | 5'-(T$_2$AG$_3$)$_4$-3' | (SEQ ID NO:13) |

Among them, ct-DNA and oligonucleotides AT, LD, and GC, can form duplexes, while oligonucleotides G10, LQ1, LQ2, LQ4, Tet12, Apt, Oxy12, Oxy28, Hum12, and Hum24 can form quadruplexes. For example, Apt can form a very stable unimolecular quadruplex with two G-quartets connected by one lateral TGT loop at one end and two parallel TT loops at the other end. Hum24 can form a unimolecular quadruplex with one diagonal T$_2$A-loop at one end and two parallel T$_2$A-loops at the other end of G-quartets. Tet12 and Hum12 can form a dimeric hairpin quadruplex with lateral loops. Oxy12 can form a dimeric hairpin quadruplex with a diagonal loop at each end of the quartets.

Carbazole compounds and their complexes with DNA duplexes and quadruplexes were studied by absorption spectroscopy, fluorescence spectroscopy, and circular dihcroism (CD):

Absorption Analysis

Each oligonucleotide described above was mixed with a solution of 10 mM Tris-HCl (pH 7.5) and 150 mM NaCl and was denatured at 90° C. for 2 min. The mixture was then cooled slowly to room temperature and stored at 4° C. for more than 2 days before use. A test compound was then added to this solution to form a compound/DNA complex. The resultant complex was subjected to absorption analysis using a Hitachi U3200 UV-visible spectrophotometer.

The absorption spectra were taken for compound 2 and its complex with each oligonucleotide. The results showed that the absorption peak of compound 2 red shifted from ~435 nm to ~450 nm in the presence of a DNA duplex and further to ~460 nm in the presence of a DNA quadruplex. In addition, the molar absorption coefficient decreased by ~15% in the presence of a DNA duplex and ~35% in the presence of a DNA quadruplex. 10 These spectra changes indicate that compound 2 binds to duplexes and quadruplexes.

Fluorescence Analysis

Compound 2 was mixed with eleven DNAs and subjected to fluorescence analysis at $\lambda_{ex}$≈430 nm, using a Hitachi F4010 spectrofluorimeter with a 2 nm bandwidth in a 1-cm cell. Fluorescence analysis was also carried out for compound 4 in the presence of Hum24. The results showed that the fluorescence of each of compounds 2 and 4 was weak in an aqueous solution. However, the fluorescence intensity unexpectedly increased in two orders of magnitude in the presence of a DNA. In addition, compound 2 exhibited a higher binding preference to a DNA quadruplex than to a DNA duplex. Further, the fluorescence peaks for a complex of compound 2 and a DNA duplex and a complex of compound 2 and a DNA quadruplex were at ~550 nm and ~575 nm, respectively.

These results suggest that compounds 2 and 4 can be used to distinguish DNA duplexes from DNA quadruplexes. In addition, these compounds possess enhanced fluorescence upon binding to DNA quadruplexes and, therefore, can be used as a biomarker for DNA quadruplexes in electrophoresis.

CD Analysis

Eight DNA quadruplexes and their complexes with compound 2 were subjected to CD analysis. CD spectra were averaged 10 scans on a Jasco J-715 spectropolarimeter with a 2 nm bandwidth. The scan speed was 50 nm/min and the step resolution was 0.2 nm.

No appreciable changes were detected in the CD spectra of DNA quadruplexes before and after compound 2 bound to them, suggesting that they were not distorted by binding with compound 2. The CD spectra also confirmed that anti-parallel quadruplexes dominate in Hum 12, Hum24, Oxy12, Oxy28, Tet12, and Apt.

Further, Hum24 and its complexes with compounds 2, 4, 6, and 8 were subjected to temperature-dependent CD analysis. The results showed that the melting temperature of Hum24 quadruplex increased in the presence of each of the four test compounds, indicating improved thermal stability.

Compound 2 and its complexes with DNA quadruplexes were further studied by polyacrylamide gel eletrophoresis (PAGE). More specifically, compound 2/DNA quadruplexes described above were analyzed by PAGE in 20% native gels in 10 mM Tris-HCl and 150 mM NaCl (pH 7.5). Gel electrophoresis was carried out in an electric field of 100 V/cm at 4° C. for 15 hours. DNA concentrations were determined by absorbencies at 260 nm and were adjusted to about 10 μM per unit structure. After photographing with UV shadowing, gels were post-stained in a solution containing 10 μM of compound 2, 10 mM Tris-HCl, and 150 mM NaCl (pH 7.5) at room temperature for 10 seconds. The gels were then rinsed by distilled water and photographed under 254 nm UV light using a digital camera.

Gels were post-stained with compound 2 after electrophoresis of AT, LD, GC, G10, LQ1, LQ2, LQ4, Tet12, Oxy12, Hum12, Apt, Oxy28, and Hum24 was complete. The results showed that that most DNAs exhibited fluorescence bands under 254 nm UV light. In particular, most DNAs migrated in the gel in a single band, but Tet12 and LQ4 migrated in two bands.

Pre-stained gels were used for selectivity assays. A 0.1 μM compound 2 solution was initially incubated with 10 μM of different DNA solutions for 10 minutes. Gel electrophoresis was then carried out in an electric field of 100 V/cm at 4° C. for 6 hours. All of the pre-stained gels were photographed under 254 nm UV light using a Bio-Rad imaging detector.

Gels pre-stained with compound 2 were used before running electrophoresis for AT, LD, GC, G10, LQ1, LQ2, LQ4, Tet12, Oxy12, Hum12, Apt, Oxy28, and Hum24. The results showed that the complexes of compound 2 and the quadruplexes of LQ2, LQ4, Oxy12, Oxy28, and Hum24 exhibited fluorescence bands under 254 nm UV light. Further, the complex of compound 2 and Tet12 quadruplex only exhibited a third fluorescence band in pre-stained gel electrophoresis, which was different from the two bands observed in post-stained gel electrophoresis. This third band is ascribed to be a linear tetramer of Tet12. On the other hand, weak fluorescence bands were detected in the complexes of compound 2 and the quadruplexes of L D, A T, Hum12, and Apt. Moreover, no fluorescence bands were detected in the complexes of compound 2 and the quadruplexes of GC, G10, and LQ1.

As mentioned above, Hum24, Oxy12, and Oxy28 contain at least one diagonal loop in their anti-parallel quadruplexes, and Apt, Tet12, and Hum12 contain no diagonal loop in their anti-parallel quadruplexes. Upon binding to compound 2, Hum24, Oxy12, and Oxy28 exhibited fluorescence bands, while Apt, Tet12, and Hum12 exhibited weak fluorescence bands resulted from anti-parallel quadruplexes. This observation suggests that compound 2 can distinguish anti-parallel quadruplexes with diagonal loops from anti-parallel quadruplexes without diagonal loops.

In addition, fluorescence was exhibited by the complexes of compound 2 and the linear tetramers of LQ2 (containing $T_2$ tails) and LQ4 (containing $T_4$ tails), but not by those of compound 2 and the linear tetramers of LQ1 (containing T tails) and G10 (containing no T tails). These results suggest that compound 2 can also distinguish linear tetramers with different lengths of T tails.

To study the sensitivity of DNA detection using electrophoresis described above, a solution containing 0.1 μM of compound 2 was incubated with solutions containing 2.5 to 0.005 μM of Hum24. The mixtures were then subjected to electrophoresis. The sensitivity assay shows that 0.1 μM of a compound 2 solution can detect the presence of 0.01 μM of Hum24 quadruplex, indicating that compound 2 is a sensitive fluorescence dye for detecting the presence of Hum24. Furthermore, the results also show that 0.1 μM of a compound 2 solution can detect the presence of 0.1 μM of LQ4 quadruplex, 0.1 μM of Oxy28 quadruplex, and a small amount of linear tetramer in 0.25 μM of Tet12 quadruplex.

EXAMPLE 10

Cancer Cell Diagnosis

A wide-field fluorescence microscopy was custom made for diagnosing cancer cells. The microscopy consists of an Ar+ laser (Coherent Inc. Santa Clara, Calif.) as the light source, a sensitive cooled charged-coupled device (CCD) camera (DV465-UV, Andor Technology, South Windsor, Conn.) for imaging, and two avalanche photodiodes (APDs) for transient photoluminescence measurement. Excitation and imaging were conducted by an oil immersion microscope objective with a numerical aperture of 1.3. A dichroism mirror (Omega) was used to direct the fluorescence into the CCD camera. A holographic notch filter (Oriel) was used to block the backscattered laser light. Images of 250×250 pixels were recorded at a high speed. The imaged area was 50×50 µm$^2$ and the spatial resolution was about 2 pixels.

The following cells were tested: CL1-1 human lung cancer cells, H1299 lung cancer cells, hTERT-BJ lung cancer cells, Ca9-22 oral cancer cells, HeLa cervical cancer cells, KJ-1 nasopharyngeal cancer cells, HaCaT keratinocyte cells, Detroit-551 skin normal cells, IMR-90 lung normal cells, and BJ-1 lung fibroblast cells. Specifically, cells were incubated with 0.1 µM of compound 2 in a culture medium for 3-6 hours. The non-fixed cells were washed three times with phosphate-buffered saline and then studied under the wide-field fluorescence microscope.

Unexpectedly, for each type of tested cancer cells, more than 70% of the cells exhibited bright fluorescence in the nucleus. By contrast, for each type of tested normal cells, only less than 20% of the cells exhibited bright fluorescence in the nucleus.

EXAMPLE 11

Cancer Cell Diagnosis by Compound 2 and Acridine Orange

Human lung CL1-0 cancer cells or MRC-5 normal cells were incubated with 0.5 µM of Compound 2 and acridine orange (AO). After incubation in standard culture medium for 1 hour, the non-fixed cells were removed by washing the culture three times with phosphate buffered saline (PBS). The fixed cells were collected in an eppendorf by trypsinization. The eppendorf was centrifuged and then illuminated by an light emitting diode (LED) emitting excitation light with a center wavelength at 470 nm. A conventional digital camera was used to record the fluorescence.

The results show that fluorescence emission was clearly observed in the eppendorf containing CL1-0 cancer cells stained with Compound 2, but no appreciable fluorescence emission was observed in the eppendorf containing MRC-5 normal cells stained with the same compound. On the other hand, fluorescence emission was detected with slight difference in intensity from both CL1-0 and MRC-5 cells stained with AO. Fluorescence emission from the cells stained with AO was brighter than those stained with Compound 2, which can be attributed to different cellular uptake.

Table 1 summarizes the numbers of cells required to distinguish cancer cells from normal cells based on fluorescence emission of Compound 2 and AO recorded by a camera under different experimental conditions. Specifically, Compound 2 and AO were incubated with four different cells in eppendorf, i.e., MRC-5 normal cells, primary fibroblast, CL1-0 cancer cells, and HeLa cancer cells. The results show that Compound 2 is a selective fluorescence dye for cancer cells.

TABLE 1

Numbers of cells required to distinguish cancer cells and normal cells by using Compound 2 and AO under different experimental conditions

| Experimental condition | Normal cells | | Cancer cells | |
| --- | --- | --- | --- | --- |
| | BMVC | AO | BMVC | AO |
| 0.5 µM/1 hr | 8,000 (M) | 2,000 (M) | 1,000 (C) | 1,000 (C) |
| 0.1 µM/1 hr | 12,500 (F) | 2,000 (F) | 2,000 (H) | 2,000 (H) |
| 0.1 µM/30 min | 10,000 (M) | 3,000 (M) | 2,000 (C) | 2,000 (C) |
| 0.05 µM/1 hr | 20,000 (F) | 4,000 (F) | 2,000 (H) | 3,000 (H) |

(M): MRC-5 normal cells,
(F): primary fibroblast,
(C): CL1-0 cancer cells,
(H): HeLa cancer cells Further, the role of the ratio of the cells stained by Compound 2/AO in cancer diagnosis was studied. Specifically, CL1-0 cancer cells, NIH3T3 normal cells, and their 1:10 mixture were respectively stained with 0.02 µM AO and 1.5 µM Compound 2 for 5 minutes in eppendorfs. Each sample was then taken from the eppendorf and spread onto a cover slip. Fluorescence emissions were recorded by a color camera upon an LED illumination. The images showed brighter fluorescence of Compound 2 in cancer cells than in normal cells. Further, the images showed 150 CL1-0 cancer cells stained with AO, ~22 CL1-0 cancer cells stained with Compound 2, and 4 NIH3T3 normal cells stained with Compound 2 showed fluorescence. In the mixture of NIH3T3 normal cells and CL1-0 cancer cells with cell ratio of 10:1, 7 cells stained with Compound 2 showed fluorescence. A statistical histogram of the ratio of the cell stained with Compound 2/AO to the ratio of the CL1-0 cells to the sum of NIH3T3 and CL1-0 cells was plotted. Each spot on the histogram represented an average of 5-10 measurements from a single sample. The histogram suggested that when the ratio of cells stained with Compound 2/AO is larger than 0.05, the patient from whom the sample is obtained should consider further examination; and when the ratio of cells stained with Compound 2/AO is larger than 0.08, the patient from which the sample is obtained requires more detailed examination by a physician.

EXAMPLE 12

Cancer Cell Diagnosis in a Tube

NIH3T3 normal cells and a mixture of NIH3T3 normal cells and CL1-0 cancer cells with a cell ratio of 100:1 were respectively stained with Compound 2 and allowed to flow through a tube. The fluorescence emission upon excitation was monitored. The results show that only weak fluorescence was observed from NIH3T3 normal cells, but bright fluorescence was observed from the mixture of NIH3T3 normal cells and CL1-0 cancer cells. The bright fluorescence was believed to be emitted from aggregation of at least 3 cancer cells in the mixture. The results suggest that cancer cells flowing in a tube have a higher chance of aggregation and therefore, if stained by Compound 2, emit brighter fluorescence upon excitation. In other words, this method can be used for early detection of cancer cells when cancer cells have a low concentration in a sample. For example, this method can be used to identify

EXAMPLE 13

Cell-based Microarray

A cell-based microarray was used to measure the detection limit of cancer cells stained with Compound 2. The microfabrication of a cell-based chip can be found in Cheng et al., J. Micromech. Microeng. (2006) 16, 1143. Briefly, microarray spots were fabricated onto glass chips by using a laser scriber. The laser direct-writing for micrometer cell pattern did not require any semiconductor-processing instruments. Cell growth was limited by the size of the spots. For example, a spot with a 20 μm diameter could only contain at most 5 cells, while a spot with a 300 μm diameter could contain several hundred cells. HeLa cells were cultured in seven different sizes of microarray spots from 800 μm to 20 μm on glass chips for 3 days and then incubated with 0.1 μM of Compound 2 for 5 hours. After each glass chip was rinsed by PBS three times, the glass chip was illuminated by an LED with a 470 nm band pass filter. The fluorescence was recorded with a conventional color camera with a 550 nm band pass filter. The results show that fluorescence emission was detected from HeLa cells stained with Compound 2 in an array having a diameter of 30 μm. Fluorescence emission was also observed from some spots of an array having a diameter of 20 μm. The results suggest that 0.1 μM Compound 2 could be used to detect the presence of less than 5 cancer cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

---

What is claimed is:

1. A device for detecting cancer cells, comprising:
a light source for generating light;
a first optical filter selected from the group consisting of a band pass filter and a long pass filter;
a second optical filter disposed between the light source and the first optical filter, the second optical filter being a band pass filter; and
a sample receiver for receiving a sample, the sample receiver being disposed between the first and second optical filters;
wherein the first optical filter, the sample receiver, and the second optical filter are aligned so that light emitted from the light source passes sequentially through the second optical filter, the sample receiver, and the first optical filter and the device does not include a detector.

2. The device of claim 1, wherein the distance between a point on the light source and a point on the second optical filter is from 5 to 7 mm.

3. The device of claim 2, wherein the distance between a point on the light source and a point on the second optical filter is from 5.5 to 6.5 mm.

4. The device of claim 1, wherein the distance between a point on the second optical filter and a point on the sample receiver is from 0.1 to 2 mm.

5. The device of claim 4, wherein the distance between a point on the second optical filter and a point on the sample receiver is from 0.5 to 1 mm.

6. The device of claim 1, wherein the distance between a point on the sample receiver and a point on the first optical filter is from 6 to 8 mm.

7. The device of claim 6, wherein the distance between a point on the sample receiver and a point on the first optical filter is from 6.5 to 7.5 mm.

8. The device of claim 1, wherein the distance between a point on the light source and a point on the second optical filter is from 5 to 7 mm, the distance between a point on the second optical filter and a point on the sample receiver is from 0.1 to 2 mm, and the distance between a point on the sample receiver and a point on the first optical filter is from 6 to 8 mm.

9. The device of claim 8, wherein the distance between a point on the light source and a point on the second optical filter is from 5.5 to 6.5 mm, the distance between a point on the second optical filter and a point on the sample receiver is from 0.5 to 1 mm, and the distance between a point on the sample receiver and a point on the first optical filter is from 6.5 to 7.5 mm.

10. The device of claim 1, wherein the first optical filter is a long pass filter.

11. The device of claim 10, wherein the first optical filter is a 520 nm long pass filter.

12. The device of claim 1, wherein the second optical filter is a 470 nm band pass filter.

13. The device of claim 1, wherein the sample receiver is planar or tubular.

14. The device of claim 13, wherein the sample receiver is a glass slide.

15. The device of claim 13, wherein the sample receiver is a tube.

16. The device of claim 15, wherein the tube has a diameter from 200 μm to 400 μm.

17. The device of claim 1, wherein the light source is a light emitting diode.

18. A device for detecting cancer cells, comprising:
a light emitting diode;
a long pass filter;
a band pass filter disposed between the light emitting diode and the long pass filter; and
a sample receiver for receiving a sample, the sample receiver being disposed between the long pass filter and the band pass filter;
wherein the long pass filter, the sample receiver, and the band pass filter are aligned so that light emitted from the light emitting diode passes sequentially through the band pass filter, the sample receiver, and the long pass filter, the distance between a point on the light emitting diode and a point on the band pass filter is from 5 to 7 mm, the distance between a point on the band pass filter and a point on the sample receiver is from 0.1 to 2 mm, the distance between a point on the sample receiver and a point on the long pass filter is from 6 to 8 mm, and the device does not include a detector.

19. The device of claim 18, wherein the long pass filter is a 520 nm long pass filter.

20. The device of claim 18, wherein the band pass filter is a 470 nm band pass filter.

21. A device for detecting cancer cells, comprising:
a light emitting diode;
a long pass filter;
a band pass filter disposed between the light emitting diode and the long pass filter; and
a sample receiver for receiving a sample, the sample receiver being disposed between the long pass filter and the band pass filter;
wherein the long pass filter, the sample receiver, and the band pass filter are aligned so that light emitted from the light emitting diode passes sequentially through the band pass filter, the sample receiver, and the long pass filter, the distance between a point on the light source and a point on the band pass filter is from 5.5 to 6.5 mm, the distance between a point on the band pass filter and a point on the sample receiver is from 0.5 to 1 mm, the distance between a point on the sample receiver and a point on the long pass filter is from 6.5 to 7.5 mm, and the device does not include a detector.

22. The device of claim 21, wherein the long pass filter is a 520 nm long pass filter.

23. The device of claim 21, wherein the band pass filter is a 470 nm band pass filter.

24. A device for detecting cancer cells, comprising:
a light source for generating light;
a first optical filter selected from the group consisting of a band pass filter and a long pass filter;
a second optical filter disposed between the light source and the first optical filter, the second optical filter being a band pass filter; and
a sample receiver for receiving a sample;
wherein the first optical filter, the sample receiver, and the second optical filter are aligned so that light emitted from the light source passes sequentially through the second optical filter and the sample receiver, at least a portion of light emitted from the sample receiver passes through the first optical filter, and the device does not include a detector.

25. The device of claim 1, further comprising a compound supported by the sample receiver, the compound having formula (I):

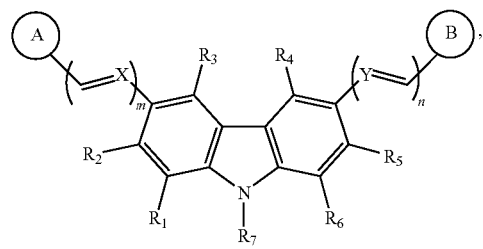

in which
each of rings A and B, independently, is heteroaryl containing at least one nitrogen atom;
each of X and Y, independently, is CH or N;
each of $R_1$-$R_6$, independently, is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl, OH, $C_1$-$C_6$ alkoxy, aryloxy, heteroaryloxy, $NH_2$, $C_1$-$C_6$ alkylamino, $C_1$-$C_{12}$ dialkylamino, arylamino, diarylamino, or halogen;
$R_7$ is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl; and
each of m and n, independently, is 1, 2, or 3.

26. The device of claim 18, further comprising a compound supported by the sample receiver, the compound having formula (I):

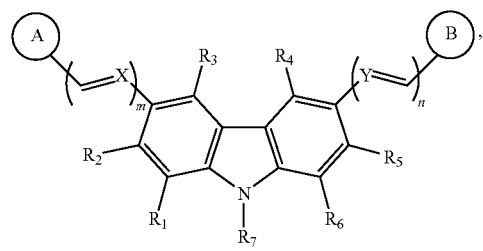

in which
each of rings A and B, independently, is heteroaryl containing at least one nitrogen atom;
each of X and Y, independently, is CH or N;
each of $R_1$-$R_6$, independently, is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl, OH, $C_1$-$C_6$ alkoxy, aryloxy, heteroaryloxy, $NH_2$, $C_1$-$C_6$ alkylamino, $C_1$-$C_{12}$ dialkylamino, arylamino, diarylamino, or halogen;
$R_7$ is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl; and
each of m and n, independently, is 1, 2, or 3.

27. The device of claim 21, further comprising a compound supported by the sample receiver, the compound having formula (I):

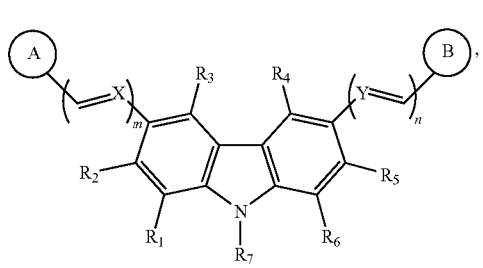
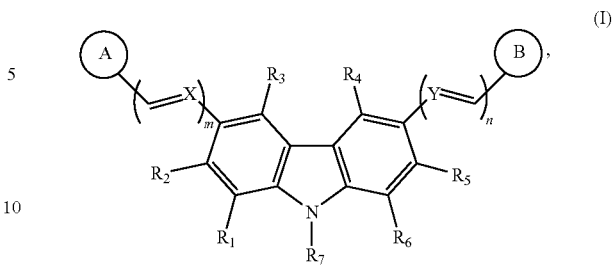

in which
each of rings A and B, independently, is heteroaryl containing at least one nitrogen atom;
each of X and Y, independently, is CH or N;
each of $R_1$-$R_6$, independently, is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl, OH, $C_1$-$C_6$ alkoxy, aryloxy, heteroaryloxy, $NH_2$, $C_1$-$C_6$ alkylamino, $C_1$-$C_{12}$ dialkylamino, arylamino, diarylamino, or halogen;
$R_7$ is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl; and
each of m and n, independently, is 1, 2, or 3.

28. The device of claim 24, further comprising a compound supported by the sample receiver, the compound having formula (I):

in which
each of rings A and B, independently, is heteroaryl containing at least one nitrogen atom;
each of X and Y, independently, is CH or N;
each of $R_1$-$R_6$, independently, is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl, OH, $C_1$-$C_6$ alkoxy, aryloxy, heteroaryloxy, $NH_2$, $C_1$-$C_6$ alkylamino, $C_1$-$C_{12}$ dialkylamino, arylamino, diarylamino, or halogen;
$R_7$ is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl; and
each of m and n, independently, is 1, 2, or 3.

\* \* \* \* \*